(12) United States Patent
Koltz, Jr. et al.

(10) Patent No.: US 12,193,723 B2
(45) Date of Patent: Jan. 14, 2025

(54) ELECTROSPUN ELECTRODE COATING

(71) Applicant: Conmed Corporation, Utica, NY (US)

(72) Inventors: Michael L. Koltz, Jr., Jacksonville, FL (US); Derek Eilers, Denver, CO (US)

(73) Assignee: Conmed Corporation, Utica, NY (US)

( * ) Notice: Subject to any disclaimer, the term of this patent is extended or adjusted under 35 U.S.C. 154(b) by 223 days.

(21) Appl. No.: 16/852,887

(22) Filed: Apr. 20, 2020

(65) Prior Publication Data
US 2020/0330149 A1  Oct. 22, 2020

Related U.S. Application Data

(60) Provisional application No. 62/836,149, filed on Apr. 19, 2019.

(51) Int. Cl.
*A61B 18/14* (2006.01)
*A61B 18/00* (2006.01)
*A61B 18/12* (2006.01)

(52) U.S. Cl.
CPC ...... *A61B 18/1442* (2013.01); *A61B 2018/00065* (2013.01); *A61B 2018/0013* (2013.01); *A61B 2018/00136* (2013.01); *A61B 2018/00345* (2013.01); *A61B 2018/00589* (2013.01); *A61B 2018/00601* (2013.01); *A61B 2018/1253* (2013.01); *A61B 2018/126* (2013.01)

(58) Field of Classification Search
CPC ...... A61B 18/1442; A61B 2018/00065; A61B 2018/0013; A61B 2018/00136; A61B 2018/00345; A61B 2018/00404; A61B 2018/00589; A61B 2018/00601; A61B 2018/1253; A61B 2018/126
USPC .............. 606/51–52, 169, 205–207
See application file for complete search history.

(56) References Cited

U.S. PATENT DOCUMENTS

| | | | | |
|---|---|---|---|---|
| 6,086,586 A * | 7/2000 | Hooven | ............ | A61B 18/1442 606/50 |
| 2004/0116792 A1* | 6/2004 | Nesbitt | ............ | A61L 31/10 606/49 |
| 2005/0171535 A1* | 8/2005 | Truckai | ............ | A61B 18/1445 606/51 |
| 2007/0129726 A1* | 6/2007 | Eder | ............ | A61B 18/1442 606/49 |
| 2010/0233115 A1* | 9/2010 | Patel | ............ | A61L 15/26 425/174.8 E |
| 2010/0241204 A1* | 9/2010 | Scheuermann | ............ | A61N 1/056 607/116 |
| 2017/0238991 A1* | 8/2017 | Worrell | ............ | H05K 1/034 |

* cited by examiner

*Primary Examiner* — Khadijeh A Vahdat
(74) *Attorney, Agent, or Firm* — Bond, Schoeneck & King PLLC; David L. Nocilly

(57) ABSTRACT

An electrosurgical device having a pair of jaws, at least one electrode supported by one of the pair of jaws, and a polymer mat positioned in covering relation a portion of the at least one electrode. The polymer mat comprises a plurality of polymer fibers having an average width of between 1 and 100 micrometers. The polymer mat has a porosity of between 6E-10m2 and 2.5E-7m2. Between 10 and 90 percent of the electrode may be exposed.

10 Claims, 3 Drawing Sheets

ELECTROSPUN ELECTRODE COATING

CROSS-REFERENCE TO RELATED APPLICATIONS

The present application claims priority to U.S. Provisional Application No. 62/836,149, filed on Apr. 19, 2019.

BACKGROUND OF THE INVENTION

1. Field of the Invention

The present invention relates to electrosurgical instruments and, more specifically, to a polymer mat coating for reducing adhesion of tissue to the electrodes of the electrosurgical device.

2. Description of the Related Art

Electrosurgical vessel sealers have become a commonly used tool for surgical procedures. A vessel sealer works by delivering electromagnetic energy to one or more electrodes to perform cutting and/or coagulation of tissue to be treated. Adhesion of the tissue that is being treated to the electrodes of the electrosurgical device often presents a problem, however, and can lead to undesirable tissue damage. Accordingly, there is a need in the art for an approach that can reduce the potential for adhesion of tissue to the electrodes of electrosurgical devices.

BRIEF SUMMARY OF THE INVENTION

The present invention is an irregular, non-patterned polymer mat coating that is applied to the electrode of an electrosurgical instrument. The coating has a low surface energy with non-stick properties and thus is suitable for reducing adhesion of the electrosurgical instrument to tissue being treated by the electrode of the instrument.

In one embodiment, the invention is an electrosurgical device having a pair of jaws, at least one electrode supported by one of the pair of jaws, and a polymer mat positioned in covering relation a portion of the at least one electrode, wherein the polymer mat comprises a plurality of polymer fibers having an average width of between 1 and 100 micrometers. The polymer mat has a porosity of between $6 \times 10^{-10}$ m$^2$ and $2.5 \times 10^{-7}$ m$^2$. Between 10 and 90 percent of the electrode may be exposed.

In another embodiment, the invention is a method of coating an electrosurgical device. A first step involves providing an electrosurgical device having a pair of jaws and at least one electrode supported by one of the pair of jaws. Another step involves positioning a polymer mat in covering relation a portion of the at least one electrode, wherein the polymer mat comprises a plurality of polymer fibers having an average width of between 1 and 100 micrometers. The polymer mat may have a porosity of between $6 \times 10^{-10}$ m$^2$ and $2.5 \times 10^{-7}$ m$^2$ and between 10 and 90 percent of the electrode may be exposed. The step of positioning a polymer mat in covering relation a portion of the at least one electrode may comprise the step of electrospinning a polymer solution to form the plurality of polymer fibers.

In a further embodiment, the invention is a method of preventing the adhesion of tissue to an electrosurgical device. A first step involves providing an electrosurgical device having a pair of jaws, at least one electrode supported by one of the pair of jaws, and a polymer mat in covering relation a portion of the at least one electrode, wherein the polymer mat comprises a plurality of polymer fibers having an average width of between 1 and 100 micrometers. A second step involves closing the electrosurgical device about a portion of tissue to be treated. A third step involves energizing the electrosurgical device to accomplish a surgical procedure without adhesion of the tissue to the electrode. The polymer mat may have a porosity of between $6 \times 10^{-10}$ m$^2$ and $2.5 \times 10^{-7}$ m$^2$, and between 10 and 90 percent of the electrode may be exposed.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
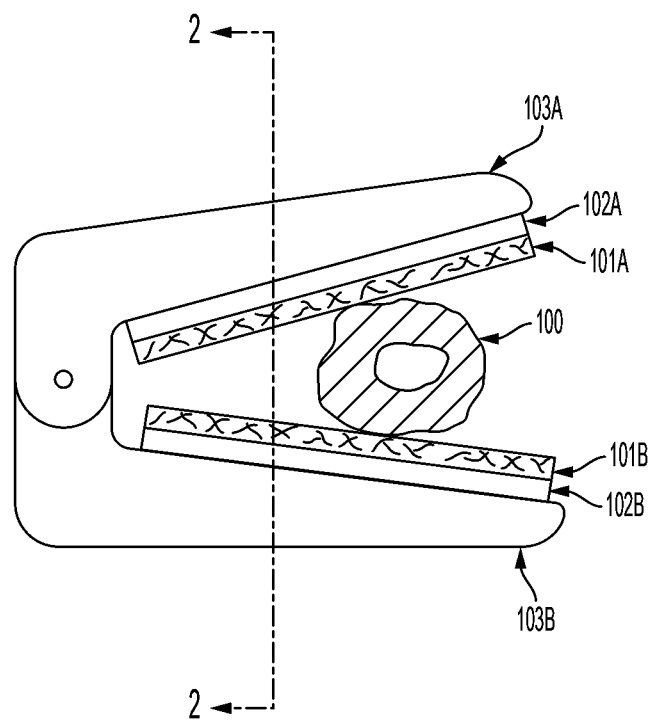
FIG. 1 is a schematic of a pair of jaws of an electrosurgical instrument that have been coated according to the present invention.
Figure 2:
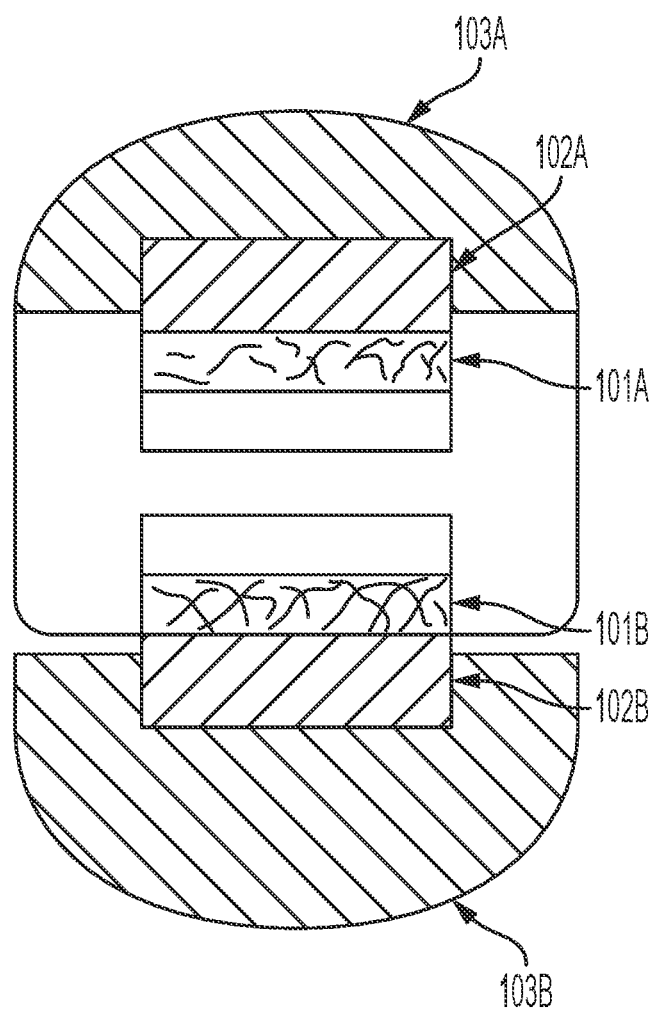
FIG. 2 is a cross-sectional schematic of a pair of jaws of an electrosurgical instrument that have been coated according to the present invention.
Figure 3:
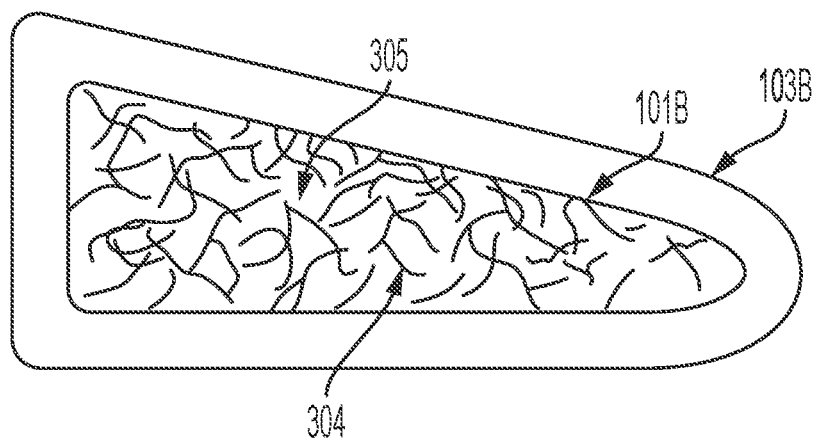
FIG. 3 is a top plan for an electrode of an electrosurgical instrument that has been coated according to the present invention.

Referring to the figures, wherein like numeral refer to like parts throughout, there is seen in FIG. 1 an electrosurgical instrument 10 shown as a portion of vessel sealing device having a pair of jaws 103A and 103B that carry a corresponding pair of electrodes 101A and 101B. Electrodes 101A and 101B have been coated according to the present invention to include corresponding coating layers 101A and 101B. As is known in the art, jaws 103A and 103B are closed about a vessel 100 and electrodes 101A and 101B energized to perform cutting and/or coagulation procedures. For example, bipolar and monopolar configured electrodes 102A and 102B may be used to transmit radio-frequency energy to soft tissues once the jaws 103A and 103B are closed about a vessel 100.

Coating layers 101A and 101B comprise a polymer mat formed from polymer fibers (304) having an average width between 1 and 100 micrometers. The thickness of the polymer mat is formed by building up layers of polymer fibers 304 to a total thickness of between 2 micrometers and 200 micrometers. The effective porosity of the polymer mat, i.e., the area between strands (305) is between $6 \times 10^{-10}$ m$^2$ and $2.5 \times 10^{-7}$ m$^2$. The percentage of the electrode exposed directly to the tissue is therefore between 10 and 90 percent. Acceptable polymer materials would include fluoropolymers and silicones. Exemplary fluoropolymers include polytetrafluoroethylene (PTFE), ethylene tetrafluoroethylene (ETFE), ethylene chlorotrifluoroethylene (ECTFE), and polyvinylidene difluoride (PVDF). Exemplary silicones include polydimethylsiloxane (PDMS).

Coating layers 101A and 101B are formed by electrospinning where a polymer solution is sprayed in liquid form onto a substrate having a differing electrical potential. The polymer may be a constituent of a solvent or in a melted state, and the appropriate electrical charges and general process known in the art of electrospinning. Electrospinning involves the use of a syringe pump for delivering a polymer solution through the metallic needle of a syringe. The metallic needle and a metal collector or substrate are coupled to a high voltage supply so that a charged jet expelled from needle can be collected on the metal collector. As is known in the art, the flow rates and voltages used to electrospin the fibers may be varied to adjust the formation of fibers on the substrate. The physical structure of the resulting fibers is approximately circular in cross section, and uniform in diameter having random curvature along their length. Individual fibers are oriented randomly relative to each other.

Coating layers 101A and 101B have non-stick properties while partially exposing the conductive surface of electrodes 102A and 102B without the need for discrete patterns or a masking step, which add complexity and expense to the coating application and removal process. Electrospun mat coatings are inherently non-patterned. As a result, the use of this approach to form electrodes 102A and 102B avoid the need for patterning tools or patterning process steps. Additionally, the width of polymer fibers 304, percent electrode coverage, and overall coating thickness can easily and precisely be controlled by process equipment settings rather than having to create of modify any hard tooling.

What is claimed is:

1. An electrosurgical device, comprising:
   a pair of jaws that are closeable about a vessel to be treated;
   at least one electrode supported by one of the pair of jaws and configured to transmit radiofrequency energy to the vessel closed in the jaws in a surgical procedure selected from the group of cutting and coagulation; and
   a mat formed by a plurality of layers and positioned in covering relation to a portion of the at least one electrode that is exposed to the vessel when the pair of jaws are closed about the vessel, wherein each of the plurality of layers is formed by a plurality of fibers, and wherein the plurality of fibers are formed from a polymer and have an average width of between 1 and 100 micrometers.

2. The electrosurgical device of claim 1, wherein the area between the polymer fibers of the polymer mat is between $6 \times 10^{-10}$ m$^2$ and $2.5 \times 10^{-7}$ m$^2$.

3. The electrosurgical device of claim 1, wherein between 10 and 90 percent of the at least one electrode is exposed.

4. A method of coating an electrosurgical device, comprising the steps of:
   providing an electrosurgical device having a pair of jaws and at least one electrode supported by one of the pair of jaws, wherein the electrode is configured to transmit radiofrequency energy to the vessel closed in the jaws in a surgical procedure selected from the group of cutting and coagulation; and
   positioning a mat formed by a plurality of layers in covering relation to a portion of the at least one electrode, wherein each of the plurality of layers is formed by a plurality of fibers, and wherein the plurality of fibers are formed from a polymer and have an average width of between 1 and 100 micrometers.

5. The method of claim 4, wherein the area between the polymer fibers of the polymer mat is between $6 \times 10^{-10}$ m$^2$ and $2.5 \times 10^{-7}$ m$^2$.

6. The method of claim 5, wherein between 10 and 90 percent of the at least one electrode is exposed.

7. The method of claim 4, wherein the step of positioning a polymer mat in covering relation to a portion of the at least one electrode comprising the step of electrospinning a polymer solution to form the plurality of polymer fibers.

8. A method of preventing the adhesion of tissue to an electrosurgical device, comprising the steps of:
   providing an electrosurgical device having a pair of jaws, at least one electrode supported by one of the pair of jaws, and a mat formed by a plurality of layers, wherein each of the plurality of layers is formed by a plurality of fibers, wherein the mat is positioned in covering relation a portion of the at least one electrode, wherein the plurality of fibers are formed from a polymer and have an average width of between 1 and 100 micrometers, and wherein the electrode is configured to transmit radiofrequency energy to the vessel closed in the jaws in a surgical procedure selected from the group of cutting and coagulation;
   closing the electrosurgical device about a portion of tissue to be treated; and
   energizing the electrosurgical device with radiofrequency energy to accomplish a surgical procedure selected from the group of cutting and coagulation without adhesion of the tissue to the electrode.

9. The method of claim 8, wherein the area between the polymer fibers of the polymer mat is between $6 \times 10^{-10}$ m$^2$ and $2.5 \times 10^{-7}$ m$^2$.

10. The method of claim 9, wherein between 10 and 90 percent of the at least one electrode is exposed.

* * * * *